United States Patent [19]

Sakurai et al.

[11] 4,362,159

[45] Dec. 7, 1982

[54] TAMPON

[75] Inventors: Akira Sakurai, Utsunomiya; Hiroshi Mizutani, Yachiyo, both of Japan

[73] Assignee: Kao Soap Co., Ltd., Tokyo, Japan

[21] Appl. No.: 309,542

[22] Filed: Oct. 7, 1981

[30] Foreign Application Priority Data

Oct. 15, 1980 [JP]  Japan ................................. 55-144164

[51] Int. Cl.$^3$ .............................................. A61F 13/20
[52] U.S. Cl. ..................................... 128/285; 428/220; 428/280; 428/288; 428/357; 428/392; 428/397; 428/401; 428/913

[58] Field of Search ............... 428/220, 280, 397, 364, 428/401, 297, 357, 913, 288, 392; 128/270, 285, 296

[56]   References Cited

PUBLICATIONS

Man–Made Fibers, vol. 2, 1968, pp. 33–42, Von Bucher.

*Primary Examiner*—James J. Bell
*Attorney, Agent, or Firm*—Flynn, Thiel, Boutell & Tanis

[57]    ABSTRACT

A tampon comprising an absorbent formed by compression molding of fibers having (A) a dry strength of at least 4.0 g/d (grams/denier), (B) a wet strength of at least 3.0 g/d, (C) a wet strength at a 5% elongation of at least 1.0 g/d, and (D) a wet elongation lower than 3.0% under a load of 0.5 g/d.

6 Claims, No Drawings

TAMPON

The present invention relates to a tampon possessing excellent absorbing properties.

With respect to the mode of application, a tampon, as a sanitary product for disposal of menses blood, is distinguished from a sanitary napkin, as an outer application type sanitary article, in that a tampon is inserted into the body to absorb menses blood. By virtue of this characteristic, tampons avoid various disadvantages of sanitary napkins, such as bulkiness at the time of application and restrictions on swimming and bathing, and tampons are effective for ensuring an active life for the wearer during menstruation.

Accordingly, the ratio of use of tampons relative to all sanitary articles for absorbing menstrual discharges has recently been increasing, and in many foreign countries, the degree of use of tampons exceeds the degree of use of sanitary napkins.

Tampons, which are now commonly used because of the reasonable absorbability thereof, still involve various problems with respect to their absorbing properties.

For example, because of an insufficient absorption capability inherent in the material of the absorbent or the low speed of penetration or diffusion of menses blood into the absorbent during absorption of menses blood, it sometimes happens that the intended absorption does not sufficiently occur and menses blood leaks out from the absorbent. This is the main disadvantage of the tampon and users complain about the insufficient absorption qualities of tampons.

This disadvantage will now be analyzed.

Absorbent cotton or rayon fibers are ordinarily used as the absorbing material of a tampon. When such a material is formed into an absorbent having a diameter of 10 to 12 mm and a length of 40 to 45 mm, in order to absorb and diffuse menses blood sufficiently into the interior of the absorbent, the ratio of the weight of the formed absorbent to the volume thereof, that is, the density of the absorbent, should be up to about 0.5 g/cm$^3$. Under this condition, the weight of the absorbent material is from 1.3 to about 2 g and it is believed that the amount of the menstrual discharge that can be absorbed by such a tampon is insufficient.

As a simple method for increasing the quantity of menstrual discharge that can be absorbed, there can be considered a method in which the weight of the material is increased. However, in this method, if it is intended to maintain the above-mentioned size of the absorbent, even though the amount of menstrual discharge absorbed is increased to some extent, the density of the absorbent is increased above 0.5 g/cm$^3$, and for that reason, the absorption or diffusion of menses blood into the absorbent is drastically inhibited. In other words, the absorption speed is reduced and, on fast discharge of menses blood, it is impossible for the absorbent to promptly absorb and hold the menses blood, with the result being that some menses blood flows between the outer surface of the absorbent and the inner wall of the vagina and leaks out from the body. Accordingly, this method is not effective.

When the weight of the material is increased while maintaining the density of the absorbent at 0.5 g/cm$^3$ or less, the absorption quantity is increased substantially in proportion to the increase of the weight of the material, and thus the final volume of the absorbent should naturally also be increased. Because of this, resistance to insertion of the tampon at the time of application is increased, and a user is apt to feel discomfort. Therefore, this method is also defective.

Under these circumstances, the latter method of increasing both the size and weight of the tampon is reluctantly adopted for tampons in order to take the absorption properties into account. In other words, in tampons formed using conventional materials, such as rayon or absorbent cotton, it is difficult to design and commercialize a small tampon which possesses excellent absorption properties and which eliminates or reduces discomfort at the time of insertion.

Studies have recently been conducted with a view to solving the foregoing problems, and results of these studies have been reported.

As one typical method, there can be mentioned a method in which the above problems are solved by increasing the absorption speed through the use of a specific material as the absorbent. For example, methods using a carboxymethylated material, a highly absorbing polymer or the like, as the absorbent material, have been tried.

Tampons obtained according to these methods apparently have greater absorption properties than tampons made of the conventional materials, but in many cases, the absorption speed is reduced relative to absorption speeds of conventional materials. The result is that, under certain application conditions, because the absorption speed is low, menses blood leaks out from the body between the absorbent and the inner wall of the vagina even though a portion of the absorbent is not saturated with menses blood. Therefore, the increased absorption properties of tampons made from these materials are ineffectively utilized in actual applications.

Furthermore, in tampons utilizing a highly absorbent processed material or a highly absorbent polymer, a water-soluble substance or a substance which is liable to separate from the absorbent proper is mainly used, and it is recognized that such substances will be dissolved and left in the body, which raises problems concerning safety.

As will readily be understood from the foregoing discussion, none of the tampons now available can simultaneously satisfy the requirements of absorption capacity, comfort and safety at the time of application.

The present inventors have conducted studies with the aim of eliminating the foregoing defects of conventional tampons, and have formed tampon-shaped absorbents using various materials and have made examinations on the absorption characteristics of these absorbents and the relations of these characteristics to the physical properties of the fibers. We discovered that a material having certain inherent fiber properties displays an excellent absorption capacity as a tampon absorbent. The present invention has now been completed based on this discovery.

More specifically, in accordance with the present invention, there is provided a tampon comprising an absorbent formed by compression molding of fibers, said fibers having the following combination of properties, namely, (A) a dry strength of at least 4.0 grams/denier (g/d), (B) a wet strength of at least 3.0 g/d, (C) a wet strength at a 5% elongation of at least 1.0 g/d, and (D) a wet elongation lower than 3.0% under a load of 0.5 g/d.

In the present invention, the absorption speed is regarded as being an important factor, and the absorbent of the tampon, according to the present invention, has a sufficient absorption speed such that, under actual application conditions, the absorbent can cope with rapid discharge of menses blood to prevent menses blood from flowing between the absorbent and the inner wall of the vagina and thereby prevent leaking from the body. The absorption speed of the absorbent, according to the invention, is comparable to that of absorbent cotton having a high absorption speed. This high absorption speed has a good effect on the quantity of menses blood that is absorbed. Accordingly, a tampon having better absorption properties than a tampon made of absorbent cotton or other conventional absorbent materials can be provided by the present invention.

The tampon of the present invention is characterized in that a material made of fibers having the above-mentioned specific properties is used as the absorbent. When the dry strength of the fibers constituting the absorbent is lower than 4.0 g/d, the absorption speed is comparable to that of ordinary rayon or absorbent cotton and good results can be obtained with respect to absorption speed, but the quantity of menses blood absorbed is reduced to the level of ordinary rayon or absorbent cotton, and thus good results cannot be obtained with respect to the quantity absorbed.

If the wet strength of the fibers is reduced to a level of about 1.5 g/d, which is the level of conventional rayon, from a relatively high level of about 3.5 g/d, which is the level of absorbent cotton, both the quantity absorbed and the absorption speed are reduced. The wet strength of the fibers, according to the invention, should preferably be at least 3.0 g/d. When the wet strength at a 5% elongation is lower than 1.0 g/d, both the absorption speed and the quantity absorbed are reduced, and in particular, the quantity absorbed is drastically reduced to the level of conventional rayon or absorbent cotton and good results cannot be obtained.

The wet elongation (%) under a load of 0.5 g/d is a factor having a most significant influence on the quantity of menses blood absorbed. If this elongation exceeds 3.0%, the quantity absorbed is reduced to the level of absorbent cotton or conventional rayon and good results cannot be obtained.

As will be apparent from the foregoing description, in the present invention the physical properties of the fibers, such as the dry strength, wet strength, wet strength at a 5% elongation and wet elongation under a load of 0.5 g/d are critical. Good results can be obtained when these physical properties are maintained within the ranges specified in the present invention.

Conventional rayon and absorbent cotton will now be compared with the absorbent material of the present invention with respect to those physical properties.

The above-mentioned physical properties of conventional rayon do not fall within the above-mentioned ranges of the present invention and the absorption capacity thereof is low. The wet strength of absorbent cotton is high and falls within the range specified in the present invention, and absorbent cotton is considered satisfactory as to this property. However, absorbent cotton is insufficient in the other physical properties required, that is, in dry strength, wet strength at a 5% elongation and wet elongation under a load of 0.5 g/d. Accordingly, the absorbent material of absorbent cotton is not satisfactory in absorption capacity.

The material of the present invention can be used in customary processing methods for preparing tampons and with treatments customarily applied to other absorbent materials, and no problems or disadvantages are caused in such processes.

For example, the absorbent material of the present invention adapts well to a lap-forming operation by a carding machine (floss lapping or lengthwise airing array), a needle punching operation, an oiling treatment and the like.

In forming the absorbent material into a tampon, there is most effectively adopted a method in which at least two starting webs are laminated so that the crossing points of the central lines are aligned with each other and the laminate is shaped in the form of a petal with the center being at the other end. Of course, the effects of the material can fully be exerted even if other forming methods are adopted.

The fineness of the fibers constituting the absorbent of the tampon also has an influence on the absorption capacity of the tampon. When a conventional absorbent material is used, the following relation is established between the fineness of the fibers and the absorption quantity and absorption speed. When the fibers are made more fine, the absorption capacity increases, and when the fibers are made less fine, the absorption speed increases.

This relationship will now be described in detail. In the case of conventional rayon fiber absorbent, a fineness of smaller than 1.5 denier is preferred from the viewpoint of the absorption quantity, but a fineness of greater than 5 denier is preferred from the viewpoint of the absorption speed. As can be seen from the foregoing, in the case of conventional materials, it is difficult to establish a fineness range wherein both the absorption quantity and the absorption speed are satisfactory. By contrast, in the material of the absorbent of the tampon employed in the present invention, a fineness of not more than 3 denier is preferred from the viewpoint of the absorption quantity and a fineness of at least 1.2 denier is preferred from the viewpoint of the absorption speed. Thus, if the fineness is in the range of from 1.25 to 3 denier, both the absorption capacity and the absorption speed are satisfactory.

Any type of fiber having the above-mentioned combination of physical properties, namely, (A) through (D), can be used as the absorbent of the present invention. However, synthetic fibers made of a polymer having a degree of polymerization of at least 450, especially polynosic rayon, are preferred in the present invention. Also, the cross-sectional shape of the fibers has an influence on the absorption capacity. When fibers having a cross section including concavities are used, the absorption capacity can be further improved.

The present invention will now be further described in more detail with reference to the following illustrative examples. In these examples, the absorption characteristics were evaluated according to the following methods.

(1) Absorption Quantity

It is considered that the absorptivity of a tampon at the time of actual use is accomplished under a so-called vagina pressure in the vagina. Accordingly, a model for measuring the absorption quantity was constructed so that a pressure of 12 g/cm$^2$, corresponding to vagina pressure, was applied to the periphery of the test sample, and this model was used for the measurement of the absorption quantity. Artificial blood having viscosity, surface tension and other physical properties similar to those of actual menses blood was used as the liquid to be absorbed.

(2) Absorption Speed

The absorption speed was determined according to the test method set forth in the Tampon Standards established by the Japanese Welfare Ministry. The same artificial blood as described above with respect to the absorption quantity measurement was used as the liquid to be absorbed. As the criterion for evaluating the absorption speed, the time required for absorption of 5 cc of the artificial blood was adopted.

under a load of 0.5 g/d of about 7.0% and about 3.0%, respectively.

In this example, a man-made fiber of polynosic rayon having an average degree of polymerization of 460 was used as the fiber material of the present invention. This polynosic rayon fiber was characterized by (A) a dry strength of at least 4.0 g/d, (B) a wet strength of at least 3.0 g/d, (C) a wet strength at a 5% elongation of at least 1.0g/d and (D) a wet elongation under a load of 0.5 g/d of less than 3.0%.

TABLE 1

|  | Description of Fibers | Dry Strength (g/d) | Wet Strength (g/d) | Wet Strength (g/d) at 5% Elongation | Wet Elongation (%) under Load of 0.5 g/d | Absorption Quantity (g) | Absorption Time (seconds) |
|---|---|---|---|---|---|---|---|
| Comparative Materials |  |  |  |  |  |  |  |
| Viscose Rayon Supplied by Company A | 1.5 D × 51 mm | 2.5 | 1.5 | 0.3 | 7.0 | 8.3 | 18 |
|  | 3 D × 51 mm | 2.1 | 1.3 | 0.4 | 6.8 | 8.0 | 15 |
|  | 5 D × 51 mm | 2.0 | 1.4 | 0.3 | 7.3 | 7.8 | 11 |
| Bemberg Rayon Supplied by Company B | 2 D × 51 mm | 2.3 | 1.6 | 0.3 | 7.4 | 8.1 | 14 |
| Absorbent Cotton Supplied by Company C | (1) | 3.3 | 3.8 | 0.9 | 2.9 | 8.5 | 8 |
|  | (2) | 3.5 | 3.7 | 0.9 | 3.3 | 8.7 | 8 |
| Absorbent Cotton Supplied by Company D |  | 3.1 | 3.5 | 1.1 | 3.1 | 8.8 | 7 |
| Materials of Present Invention |  |  |  |  |  |  |  |
| A-1 | 1.25 D × 51 mm | 4.2 | 3.2 | 1.4 | 1.8 | 10.3 | 10 |
| A-2 | 1.5 D × 51 mm | 4.0 | 3.0 | 1.0 | 3.0 | 10.3 | 8 |
| A-3 | 1.5 D × 51 mm | 4.5 | 3.4 | 1.5 | 2.0 | 10.0 | 8 |
| A-4 | 3 D × 64 mm | 4.4 | 3.5 | 1.2 | 2.3 | 9.7 | 6 |
| A-5 | 5 D × 51 mm | 4.3 | 3.3 | 1.2 | 2.5 | 8.9 | 5 |

EXAMPLE 1

Conventional rayon fibers and absorbent cotton fibers were used as the comparative conventional materials. These conventional materials and the fiber materials of the presnt invention were tested. More specifically, 2.5 g of each material was shaped into a tampon having a density of 0.5 g/cm$^3$. The absorption quantity and absorption speed of each of the samples prepared in this manner were measured according to the above-mentioned methods. The results obtained are shown in Table 1.

The conventional rayon fibers and absorbent cotton fibers used as the comparative conventional materials were characterized by (A) dry strengths of about 2.5 g/d and about 3.5 g/d, respectively, (B) wet strengths of about 1.5 g/d and about 3.5 g/d, respectively, (C) wet strengths at a 5% elongation of about 0.5 g/d and about 1.0 g/d, respectively, and (D) wet elongations As is apparent from the results shown in Table 1, the fiber materials of the present invention are superior to conventional rayon and absorbent cotton in both absorption capacity and absorption speed.

In Table 1, (1) of Description of Fibers means sanitary cotton comprising Indian cotton having 14.5 to 22 micron thickness and 12 to 20 mm length on the average. (2) means sanitary cotton comprising American cotton having 13.5 to 17 micron thickness and 16 to 30 mm length on the average.

EXAMPLE 2

In order to examine the influence of the fiber cross section, tampons differing in sectional configuration were prepared from various fibers, and the absorption capacities and absorption speeds of these tampons were measured. The results obtained are shown in Table 2. From the results shown in Table 2, it will readily be understood that if the fiber section has concavities, as in the case of an L-shaped or Y-shaped fiber section, the absorption capacity can be further improved.

TABLE 2

| Description of Fibers | Sectional Shape | Dry Strength (g/d) | Wet Strength (g/d) | Wet Strength (g/d) at 5% Elongation | Wet Elongation (%) under Load of 0.5 g/d | Absorption Quantity (g) | Absorption Time (seconds) |
|---|---|---|---|---|---|---|---|
| Comparative Materials |  |  |  |  |  |  |  |

TABLE 2-continued

| | Description of Fibers | Sectional Shape | Dry Strength (g/d) | Wet Strength (g/d) | Wet Strength (g/d) at 5% Elongation | Wet Elongation (%) under Load of 0.5 g/d | Absorption Quantity (g) | Absorption Time (seconds) |
|---|---|---|---|---|---|---|---|---|
| Bemberg Rayon Supplied by Company B | 2 D × 51 mm | L | 2.1 | 1.4 | 0.2 | 7.6 | 8.3 | 22 |
| | 3 D × 51 mm | L | 2.3 | 1.5 | 0.2 | 7.9 | 8.0 | 17 |
| Flat Hollow Rayon Supplied by Company E | 1.5 D × 51 mm | flat | 1.9 | 1.2 | 0.2 | 7.5 | 8.7 | 18 |
| | 5 D × 21 mm | flat | 2.0 | 1.1 | 0.2 | 7.3 | 8.3 | 15 |
| Flat Hollow Rayo Supplied by Company F | 2 D × 38 mm | indefinite | 1.8 | 1.1 | 0.2 | 8.1 | 10.1 | 160 |
| | 3 D × 38 mm | indefinite | 1.9 | 1.0 | 0.2 | 8.2 | 10.0 | 135 |
| Materials of Present Invention | | | | | | | | |
| B-1 | 1.5 D × 51 mm | L | 4.1 | 3.0 | 1.1 | 2.3 | 11.1 | 9 |
| B-2 | 3 D × 51 mm | L | 4.3 | 3.3 | 1.2 | 2.6 | 10.7 | 8 |
| B-3 | 5 D × 51 mm | L | 4.5 | 3.6 | 1.5 | 2.5 | 10.2 | 6 |
| B-4 | 3 D × 51 mm | Y | 4.2 | 3.3 | 1.4 | 2.3 | 10.9 | 9 |
| B-5 | 5 D × 51 mm | Y | 4.5 | 3.1 | 1.2 | 2.5 | 10.0 | 8 |
| B-6 | 1.5 D × 51 mm | flat | 4.3 | 3.2 | 1.2 | 2.6 | 11.0 | 9 |
| B-7 | 3 D × 51 mm | flat | 4.4 | 3.5 | 1.3 | 2.1 | 10.4 | 7 |

The embodiments of the invention in which an exclusive property or privilege is claimed are defined as follows:

1. In a tampon comprising an absorbent material composed of compression molded fibers, the improvement which comprises: said fibers consist essentially of polynosic rayon fibers having a dry strength of at least 4.0 g/denier, a wet strength of at least 3.0 g/denier, a wet strength at a 5% elongation of at least 1.0 g/denier and a wet elongation of not more than 3.0% under a load of 0.5 g/denier.

2. A tampon as set forth in claim 1, wherein said polynosic rayon fibers have an average degree of polymerization of at least 450.

3. A tampon as set forth in claim 1 or claim 2, wherein the fineness of said polynosic rayon fibers is in the range of from 1.25 to 3 denier.

4. A tampon as set forth in claim 1, wherein the cross section of said polynosic fibers has concavities.

5. A tampon as set forth in claim 3, wherein said polynosic rayon fibers have an L-shaped or a Y-shaped cross section.

6. A tampon according to claim 3, wherein said absorbent material has a diameter of 10 to 12 mm, a length of 40 to 45 mm and a density of about 0.5 g/cm³.

* * * * *